DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED MAY 4, 1971

886 O.G. 4

T886,004
PURIFICATION OF DIPOTASSIUM TEREPHTHALATE

Erdem M. Atadan, Wilmington, Del., assignor to E. I. du Pont de Nemours and Company, Wilmington, Del.

Filed Dec. 4, 1969, Ser. No. 882,281
Int. Cl. C07c *51/42*
U.S. Cl. 260—525
No Drawing. 7 Pages Specification

Purified dipotassium terephthalate is recovered from crude aqueous dipotassium terephthalate solution containing potassium para-toluate as an impurity bv crystallizing dipotassium terephthalate in an amount such that the weight ratio of potassium para-toluate to dipotassium terephthalate remaining in the aqueous solution does not exceed the potassium para-toluate to dipotassium terephthalate weight ratio at which potassium para-toluate will begin to crystallize, followed by separating the dipotassium terephthalate crystals from the aqueous solution, preferably by filtration. The crude aqueous solution of dipotassium terephthalate can be prepared either by dissolving crude terephthalic acid in a potassium alkaline aqueous solution, e.g., aqueous potassium hydroxide, or directly from the oxidation of para-xylene or para-toluic acid in a potassium alkaline aqueous medium. The crystallization is conducted at about from 0° to 160° C., preferably about from 10 to 140° C.. and at about from 0.1 to 10, preferably about from 0.5 to 4, atmospheres of total pressure. The dipotassium terephthalate can then be washed with any solvent which is chemically inert with respect to the dipotassium terephthalate, preferably a nearly saturated aqueous solution of dipotassium terephthalate, to displace any remaining mother liquor. Purified terephthalic acid can then be recovered by acidifying an aqueous solution of the purified dipotassium terephthalate.